(12) United States Patent
Rosselet et al.

(10) Patent No.: US 11,786,204 B2
(45) Date of Patent: *Oct. 17, 2023

(54) AUTOMATICALLY-REGISTERED PATIENT FIXATION DEVICE IMAGES

(71) Applicant: Varian Medical Systems International AG, Steinhausen (CH)

(72) Inventors: Armel C. Rosselet, Baden (CH); Xinhui Yang, Oberrohrdorf (CH); Martin Sabel, Hagendorn (CH)

(73) Assignee: Siemens Heathineers International AG, Steinhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,558

(22) Filed: Aug. 19, 2022

(65) Prior Publication Data

US 2022/0386980 A1 Dec. 8, 2022

Related U.S. Application Data

(63) Continuation of application No. 16/833,778, filed on Mar. 30, 2020, now Pat. No. 11,478,210.

(51) Int. Cl.
*A61B 6/00* (2006.01)
*A61B 6/03* (2006.01)
(Continued)

(52) U.S. Cl.
CPC .......... *A61B 6/5229* (2013.01); *A61B 6/032* (2013.01); *A61B 6/0421* (2013.01); *A61B 6/469* (2013.01); *A61N 5/1039* (2013.01)

(58) Field of Classification Search
CPC .... A61N 5/103; A61N 5/1039; A61N 5/1097; A61B 6/032; A61B 6/0421; A61B 6/469;
(Continued)

(56) References Cited

U.S. PATENT DOCUMENTS 10,376,217 B2 8/2019 Schmidt
11,406,844 B2 8/2022 Yang
(Continued)

FOREIGN PATENT DOCUMENTS

WO 2012080948 A1 6/2012
WO 2016140955 A1 9/2016
(Continued)

OTHER PUBLICATIONS

Nioutsikou, Elena et al.; Patient-Specific Planning for Prevention of Mechanical Collisions During Radiotherapy; Physics in Medicine and Biology, vol. 48, No. 22; Oct. 24, 2003; pp. N313-N321.
(Continued)

*Primary Examiner* — Boniface Ngathi N
(74) *Attorney, Agent, or Firm* — Fitch, Even, Tabin & Flannery LLP

(57) ABSTRACT

A three-dimensional model for a patient fixation device that serves to immobilize at least a portion of a particular patient when capturing CT image information of that patient is accessed and then registered with the pixels that correspond to the patient fixation device in the CT image. The model can specify rules of movement for each of a plurality of structural elements that comprise the patient fixation device and that are capable of movement relative to one another. By one approach the aforementioned registration occurs on a part-by-part basis for each of the structural elements. Following registration, the CT image can be automatically segmented.

20 Claims, 6 Drawing Sheets

(51) Int. Cl.
 *A61B 6/04* (2006.01)
 *A61N 5/10* (2006.01)

(58) Field of Classification Search
 CPC ....... A61B 6/488; A61B 6/502; A61B 6/5217; A61B 6/5229; A61B 6/5235
 See application file for complete search history.

(56) References Cited

U.S. PATENT DOCUMENTS

| | | | |
|---|---|---|---|
| 11,478,210 B2* | 10/2022 | Rosselet | ............... A61N 5/1039 |
| 2012/0201421 A1 | 8/2012 | Hartmann | |
| 2013/0142310 A1 | 6/2013 | Fahimian | |
| 2017/0086758 A1 | 3/2017 | McCarthy | |
| 2018/0000435 A1 | 1/2018 | Liu | |
| 2018/0043183 A1 | 2/2018 | Sheng | |
| 2019/0030371 A1 | 1/2019 | Han | |
| 2021/0299470 A1 | 9/2021 | Nord | |
| 2021/0299471 A1 | 9/2021 | Yang | |

FOREIGN PATENT DOCUMENTS

| | | | |
|---|---|---|---|
| WO | 2017087985 A1 | 5/2017 | |
| WO | 2017210690 A1 | 12/2017 | |

OTHER PUBLICATIONS

Zou, Wei et al., A Clinically Feasible Method for the Detection of Potential Collision in Proton Therapy; Medical Physics, vol. 39, No. 11, Nov. 2012, pp. 7094-7101.

RaySearch Laboratories: Automated Breast Planning with rayAutoBreast video from https://www.youtube.com/watch?v=jG6GvfGf4z0&t=44s posted, Nov. 18, 2014; Screen captures and transcription of audio, 10 pages.

RayStation Laboratories: RayStation Fallback Planning video from https://www.youtube.com/watch?v=8x1pTelB0LA, posted Mar. 5, 2015; Screen captures and transcription of audio, 10 pages.

Ryalat, Mohammad Hashem et al., Fast and Automatic Approach for Removing Artefacts Due to Immobilisation Masks in X-ray CT; 2017 IEEE EMBS International Conference on Biomedical & Health Informatics (BHI); 4 pages.

Locke, Christopher Barry; Bush, Karl Kenneth; Trajectory Optimization in Radiotherapy Using Sectioning (TORUS); American Association of Physicists in Medicine [https://doi.org/10.1002/mp.12270]; Med. Phys. 44(7), Jul. 2017; pp. 3375-3392.

Men, Kuo et al.; Fully Automatic and Robust Segmentation of the Clinical Target Volume for Radiotherapy of Breast Cancer Using Big Data and Deep Learning; Physica Medica, Acta Medica Edizioni E Congressi, Rome, IT; vol. 50, May 19, 2018; pp. 13-19.

\* cited by examiner

AUTOMATICALLY-REGISTERED PATIENT FIXATION DEVICE IMAGES

CROSS-REFERENCE TO RELATED APPLICATION

This application is a continuation of U.S. patent application Ser. No. 16/833,778, filed Mar. 30, 2020, now U.S. Pat. No. 11,478,210, which is hereby incorporated herein by reference in its entirety.

RELATED APPLICATIONS

This application is related to co-pending and co-owned U.S. patent application Ser. No. 16/833,752, filed Mar. 30, 2020, entitled AUTOMATICALLY-PLANNED RADIATION-BASED TREATMENT and U.S. patent application Ser. No. 16/833,801, filed Mar. 30, 2020, entitled METHOD AND APPARATUS TO DERIVE AND UTILIZE VIRTUAL VOLUMETRIC STRUCTURES FOR PREDICTING POTENTIAL COLLISIONS WHEN ADMINISTERING THERAPEUTIC RADIATION, the contents of which are fully incorporated herein by this reference.

TECHNICAL FIELD

These teachings relate generally to the use of radiation as a therapeutic treatment and more specifically to the formation and use of corresponding radiation-treatment plans that accommodate a patient fixation device.

BACKGROUND

The use of radiation to treat medical conditions comprises a known area of prior art endeavor. For example, radiation therapy comprises an important component of many treatment modalities for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan serves in the foregoing regards.

Treatment plans serve to specify any number of operating parameters as pertain to the administration of such treatment with respect to a given patient and a particular real-world physical radiation treatment platform. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

A radiation treatment plan planning workflow typically involves numerous manual and iterative steps. This is particularly so when inverse planning-based techniques, such as IMRT and VMAT, are employed. At each of a series of steps decisions/choices are made that may often affect later stages. Such factors can lead to an overly complex planning workflow when only simple 3-D planning may be necessary (for example, to develop a treatment plan to address breast cancer). In particular, a physician must often manually segment the target structures and the organs at risk via a time-consuming process that is also prone to observer variability. That variability, in turn, can be exacerbated by the field set up that must be determined manually before beginning the optimization process and by the definition of appropriate objectives for the optimizer. This segmentation activity can be further challenged with patient fixation devices are in play, as those devices are often, at least to some extent, evident in the computed tomography images that inform such activity.

Because exploring all or most possible combinations typically comprises a time-consuming and computationally expensive process, in some application settings users may opt to proceed with a simpler approach or simply a previously known practice. Making that choice, however, can greatly limit the options that may be available and suitable to consider for a particular patient.

Other limitations are also found in the prior art. For example, while one prior art approach estimates multiple scripted plans for different treatment units, those plans are not created to take collision avoidance into account and typically are neither ready for delivery nor suitably customized for a particular patient.

BRIEF DESCRIPTION OF THE DRAWINGS

The above needs are at least partially met through provision of the automatically-registered patient fixation image apparatus and methods described in the following detailed description, particularly when studied in conjunction with the drawings, wherein.

Figure 1:
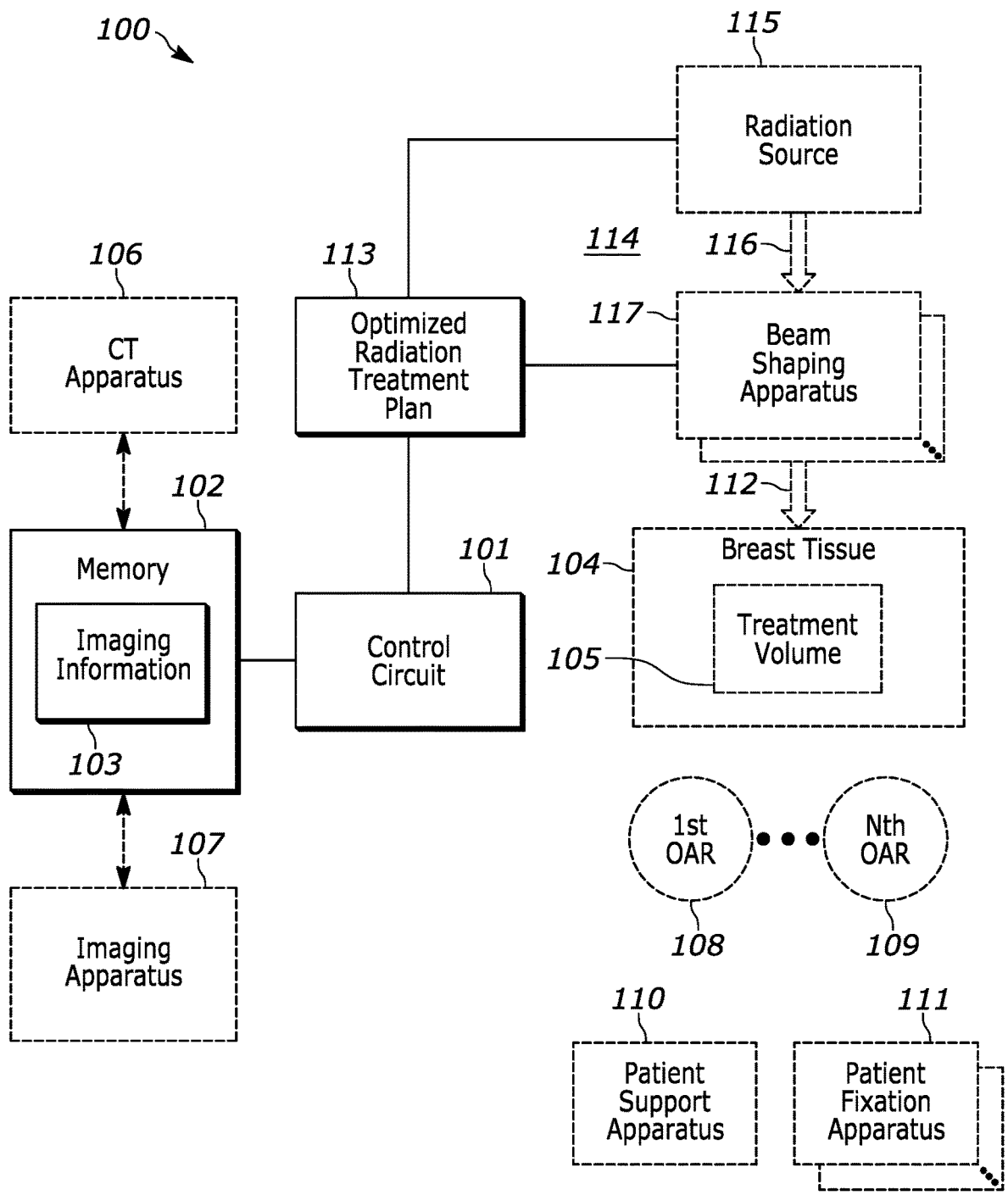
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, many of these various embodiments provide for dealing with images of patient fixation devices that appear in computed tomography image information for a particular patient.

By one approach, these teachings provide for accessing computed tomography (CT) image information for a particular patient where the CT image information includes image information regarding a fixation device that served to immobilize at least a portion of the particular patient while capturing the CT image information. In many application settings the fixation device will comprise a plurality of structural elements, at least some of which are capable of movement relative to one another.

These teachings then provide for accessing a three-dimensional (3-D) model for that fixation device and registering that 3-D model with the image information regarding the fixation device to thereby provide registered CT image information for the particular patient. The latter can then be used to automatically segment the CT image information for the particular patient to provide segmented image information for the particular patient.

By one approach, that segmented information for the particular patient can be used to prepare a radiation treatment plan for that particular patient. In addition, if desired, that radiation treatment plan for the particular patient can be used to administer corresponding therapeutic radiation to the particular patient.

By one approach the 3-D model for the fixation device includes rules that specify rules of movement for each of the plurality of structural elements that are capable of movement relative to one another. By one approach, for example, at least one such rule can specify a range of permitted movement. By another approach, and as another example, at least one of the rules of movement can specify a linear translation of a first one of the plurality of structural elements with respect to a second one of the plurality of structural elements. Such a linear translation can be characterized/defined by translation along a vector defined by two points belonging to the second one of the plurality of structural elements.

By another approach, in lieu of the foregoing or in combination therewith, at least one of the rules of movement can specify rotation of a first one of the plurality of structural elements with respect to a second one of the plurality of structural elements. As one nonlimiting example in the foregoing regards, such a rule of movement can specify rotation of the first one of the plurality of structural elements around a vector that is defined by two points belonging to the second one of the plurality of structural elements.

By one approach, registering the 3-D model for the fixation device with the image information regarding the fixation device itself can comprise, at least in part, registering the plurality of structural elements in a seriatim manner. As one example in these regards, this may begin with first registering a base plate that comprises a part of the fixation device.

So configured, a patient fixation device can be efficiently and accurately identified in a CT image containing patient information to thereby enable efficient and accurate segmenting of the contents of that CT image. Generally speaking, the teachings presented herein in these regards permit automatically identifying the patient fixation device structures in a CT image of a patient in less time than might typically be expected using prior art approaches and, perhaps just as importantly, with potentially improved accuracy.

In combination with the foregoing or in lieu thereof, these teachings will also accommodate automatically planning radiation-based treatment of a treatment volume of a particular patient. As one particularly salient example in these regards, this can comprise automatically planning radiation-based treatment of a treatment volume within the breast tissue of a particular patient. As a useful illustrative example, many or all of the activities in support of the foregoing are facilitated by use of a control circuit.

By one approach, these teachings provide for accessing imaging information for a treatment zone that includes the treatment volume of the particular patient. The control circuit can then employ that imaging information along with deep learning to automatically segment at least some breast tissue of the particular patient (and perhaps the heart) and non-deep learning to automatically segment at least portions of some organs-at-risk (such as, but not limited to, a lung, a portion of a spinal column, and a portion of a chest wall) to provide automatically segmented patient content. Atlas and model-based approaches two examples of non-deep learning approaches. Atlas-based segmentation assumes that given patient images can be segmented by propagating structures from manually-segmented atlases. The atlas image is deformed to match the patient image using one or more deformable image registration algorithms and structures are propagated using deformation vector fields mapping voxels of the atlas image to voxels of the patient image. Model-based structure segmentation delineates structure by detecting edges and points directly on patient images. Multiple image processing techniques are often employed in these regards. In many cases it will be appropriate for the user to manually define the volumes. Generally speaking these approaches combine deep learning with density and heuristic searching algorithms. The latter are existing algorithms that are sometimes employed in existing treatment planning systems. The combination of such existing density and heuristics-based tools with deep learning, however, was previously unknown to the applicant.

The control circuit can also employ that imaging information to automatically determine a virtual-skin volume that corresponds to at least portions of the foregoing breast tissue (in particular, the skin thereof). By one approach the control circuit then employs that automatically segmented patient content and the virtual-skin volume as input when automatically optimizing a radiation treatment plan for the foregoing treatment volume of this particular patient to thereby provide an optimized radiation treatment plan for this particular patient.

By one approach the foregoing imaging information includes three-dimensional computed tomography (CT) imaging information. By one approach the foregoing imaging information can further include two-dimensional topogram imaging information. In such a case, when the control circuit employs the imaging information to automatically determine the above-mentioned virtual-skin volume that corresponds to at least portions of the particular patient's breast tissue, this can comprise, at least in part, using both the three-dimensional CT imaging information and two-dimensional orthogonal topogram imaging information to determine that virtual-skin volume.

By one approach, the control circuit can also employ the imaging information along with deep learning (as versus non-deep learning) to automatically segment at least some heart tissue of the particular patient. Generally speaking, the inventors have determined that some anatomical structures, such as lungs, the spinal cord, bones, eye structures, and so forth can be easily and accurately segmented using standard non-deep learning approaches while other structures, and especially those without well-defined edges, are more problematic. In the latter regards, deep learning-based approaches can yield better results and more quickly.

In many radiation treatment application settings, the patient is supported by a patient support surface (such as, but not limited to, a couch). In some cases a patient fixation apparatus may also be employed as noted above, in lieu of the foregoing or in combination therewith, to spatially affix some part of the patient's body to thereby maintain that body part in a relatively stationary position/orientation. With this in mind, by one approach these teachings can further comprise automatically registering at least one of a patient support surface and a patient fixation apparatus to at least some of the imaging information to provide registration information and to also employ that registration information as further input when automatically optimizing the foregoing radiation treatment plan. As one nonlimiting illustrative example in these regards, the foregoing can comprise automatically registering a model of at least one of the patient support surface and the patient fixation apparatus to at least some of the imaging information.

By one approach, these teachings will further accommodate employing the foregoing imaging information to automatically determine a body outline for at least a portion of the patient. In such a case, the control circuit can then employ, for example, that body outline, the above-mentioned virtual-skin volume, and the registration information described above as inputs to automatically calculate radiation treatment platform trajectories, collision detection information, and virtual dry run information of treatment delivery per the optimized radiation treatment plan.

So configured, and by one approach, these teachings facilitate automating many of the time-consuming steps that currently discourage users from exploring alternative techniques beyond, for example, conformal radiotherapy. By one approach these teachings serve to automatically generate multiple scored plans for multiple modalities of beam-based radiation treatment. Each of these plans can include collision-free geometry definition, beam energy selection, dosimetric optimization, and dose calculation. It may also be noted that these teachings leverage deep learning to accomplish breast CT data segmentation and also feature significantly improved bolus creation and utilization as described below.

These and other benefits may become clearer upon making a thorough review and study of the following detailed description.

Before describing in greater detail the foregoing teachings, however, it may be helpful to the reader to first provide a general description of one example of a current inverse planning workflow to treat an instance of breast cancer. This example will help to exemplify that at least some current processes, while relying upon some degree of automation, necessarily makes frequent call upon human intervention, judgment calls, and oversight.

This example of a current inverse planning workflow begins with CT simulation. Such a simulation can begin by scanning that includes the breast board (which may include triangulation or leveling the patient), lead wires for the borders, and/or a wire frame for the entire breast tissue. The technician then employs CT simulation software to create the requisite 3-D image and contours.

That technician (or another), working at a suitably equipped contouring workstation, imports the foregoing CT/body content imagery information and automatically contours the information. (A volumetric modulated arc therapy (VMAT) user may also manually extend the body image to accommodate "skin flash" during optimization.) This contouring can include contouring both the left and right lungs, heart, contralateral breast, spinal cord, nodal chains, and the patient target volume (PTV).

The technician can also add bolus content if desired to increase skin dose or as a workaround for skin flash. (For VMAT the user may add bolus content to get skin flash during optimization and then remove that bolus content prior to calculating dosing.) The latter activity can include defining both the bolus thickness and the shape of the bolus (for example, by selecting a pre-defined shape or by creating a customized shape that serves, for example, to cover the complete irradiated area). (In radiation therapy, bolus is a material having properties equivalent to a given tissue, such as breast tissue, when irradiated. Bolus content is often used to reduce or alter dosing for targeted radiation therapy. Bolus content can serve, for example, to compensate for missing or irregularly shaped tissue and/or to modify radiation dosage at the skin.)

The results of the contouring process are then passed from the contouring process to an external beam planning workstation and its corresponding technician. The external beam planning process typically creates a forward plan (i.e., a base dose plan) that includes calculated and normalized parameters for a plurality of treatment fields. In some cases this activity may also include converting isodose lines to corresponding structure to obtain an optimized patient treatment volume. The specific calculations and steps for external beam planning will vary, in part, depending upon whether the plan corresponds to an IMRT plan or a VMAT plan. In some cases this planning process may also include using a skin flash tool to add flash to one or more fields.

The external beam planning process will typically work in correspondence with an optimization process to iteratively calculate the administered doses. In any event, the resultant plan is subsequently evaluated in an external beam planning (EB) or plan evaluation (PE) workstation. This evaluation can include evaluating the 100 percent isodose coverage achieved by the plan, the location of minimum and maximum dosing, and administered monitor units (MU's) (monitor unites being a measure of machine output from a clinical accelerator for radiation therapy such as a linear accelerator).

Being replete with platform handoffs and frequent or sometimes constant human attendance, such an overall process, while often capable of achieving useful results, is also time-consuming, subject to human frailty, and not intrinsically capable of achieving the potential synergy of its constituent activities.

Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

In this illustrative example the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

This memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

In this example this memory 102 can also serve to store imaging information 103. This imaging information can comprise information regarding images (such as "images" per se) for a patient's treatment zone that includes the treatment volume 105 of that particular patient. For the sake of an illustrative example it will be presumed here that this treatment volume 105 is within the breast tissue 104 of the patient.

These teachings are flexible in practice and will accommodate various kinds of imaging information. By one approach the imaging information 103 includes three-dimensional computed tomography (CT) imaging information provided, for example, by a corresponding CT apparatus 106. As another example, in lieu of the foregoing or in combination therewith, the imaging information 103 can include two-dimensional topogram imaging information provided by the CT apparatus 106 or by a corresponding suitable imaging apparatus 107. (Topograms are well understood in the art and are sometimes called a scout view or surview; topograms are two-dimensional images generated by tomography without being reconstructed into slices.)

It will also be understood that the imaging information 103 may include image information for one or more organs-at-risk (represented in FIG. 1 by a first organ-at-risk 108 through an Nth organ-at-risk 109 (where "N" is an integer greater than "1")) for the particular patient. An organ-at-risk is part or all of a non-targeted organ that is at risk of being harmed by radiation when treating the treatment volume 105 with radiation. Relevant examples of such organs-at-risk (when the treatment volume 105 is within breast tissue 104) include one or both lungs, a portion of the spinal column, and a portion of the chest wall as well as the heart.

And, it will be further understood that the imaging information 103 may also include image information for a patient support apparatus 110 (such as a so-called couch) and/or one or more patient fixation apparatuses 111 (sometimes also referred to herein as patient fixation devices 111) that serve to hold and maintain some part of the patient's body in a fixed position relative a radiation treatment beam 112.

If desired the control circuit 101 also operably couples to a network interface (not shown). So configured the control circuit 101 can communicate with other elements (both within the apparatus 100 and external thereto) via that network interface. Network interfaces, including both wireless and non-wireless platforms, are well understood in the art and require no particular elaboration here.

By another optional approach (in lieu of the foregoing or in combination therewith) the control circuit 101 may also operably couple to a user interface (not shown). This user interface can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

As is described in more detail below, the control circuit 101 is configured, at least in part, to optimize a radiation treatment plan to thereby yield one or more optimized radiation treatment plans 113. This optimized radiation treatment plan 113 serves to control a radiation treatment platform 114 that can include, for example, a radiation source 115 that can, if desired, operably couple and respond to the control circuit 101. Radiation sources are well understood in the art and require no further description here.

So configured, the corresponding radiation beam 116 emitted by the radiation source 115 can be selectively switched on and off by the control circuit 101. These teachings will also accommodate having the control circuit 101 control the relative strength of the radiation beam 116. The radiation treatment platform 114 may also be configured to move the radiation source 115 during the treatment session to thereby administer radiation from a variety of different directions ("fields"). In such a case the control circuit 101 may also be configured to control such movement.

By one optional approach, and as illustrated here, the radiation treatment platform 114 can further include one or more beam-shaping apparatuses 117. Such apparatuses 117 serve to modify the radiation beam 116 by, for example, shaping the beam 116 and/or by otherwise modulating the radiation beam to thereby yield a corresponding output radiation beam 112 to which the treatment volume 105 is exposed. Well known examples of beam-shaping apparatuses include, but are not limited to, jaws, collimators, and multi-leaf collimators.

Figure 2:
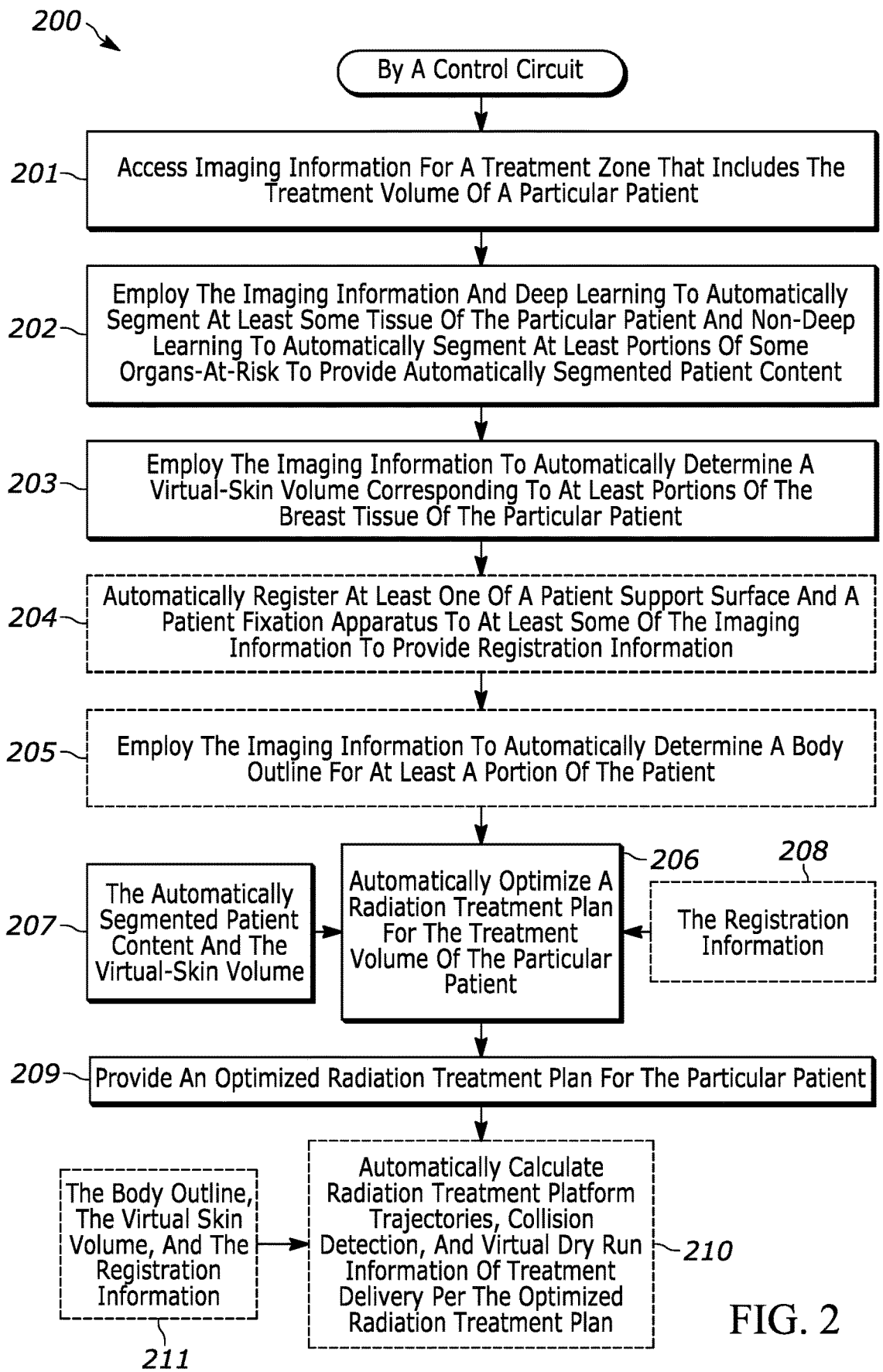
FIG. 2 comprises a flow diagram as configured in accordance with various embodiments of these teachings.

For the sake of an illustrative example it will be presumed here that the aforementioned control circuit 101, in conjunction with the above-described application setting, carries out at least some (and possibly all) of the actions, steps, and/or functions described herein. FIG. 2 presents a process 200 that accords with many of these teachings.

At block 201 this process 200 provides for accessing imaging information (such as the aforementioned imaging information 103) for a treatment zone that includes the treatment volume 105 of a particular patient. This illustrative example presumes that the treatment volume 105 is located within breast tissue 104 of this patient. Also for the sake of illustration, this example presumes that the imaging information 103 specifically includes three-dimensional CT imaging information as well as two-dimensional topogram imaging information. In addition to the treatment volume 105 itself, the imaging information 103 can comprise imaging information that includes at least portions of one or more organs at risk 108, 109 such as the patient's lung, a portion of the patient's spinal column, and/or a portion of the patient's chest wall. Also, in an appropriate application setting, the imaging information 103 can comprise imaging information for one or more of a patient support apparatus 110 and/or one or more patient fixation apparatuses 111.

By one approach one or more items of the imaging information 103 are captured at this particular time of need (i.e., at the time of preparing and optimizing a radiation treatment plan for this particular patient) and when the patient is located at the radiation treatment platform 114 itself. By another approach one or more items of the imaging information 103 are captured at an earlier time and perhaps when the patient is not located at the radiation treatment platform 114 itself.

At block 202 this process 200 provides for employing the imaging information 103 while also employing deep learning to automatically segment at least some breast tissue 104 of the particular patient and non-deep learning to automatically segment at least portions of some organs-at-risk 108, 109 to provide automatically segmented patient content. This process will also accommodate automatically segmenting any high-density artifacts in the patient's body.

By one approach this activity can include defining a body outline for the patient. In addition, or in lieu thereof, this activity can include automatically detecting and defining the positions of wires and/or radiographic markers on the patient's body surface. So detected and defined, this activity can then include automatically removing that specific content from the 3-D CT image.

Segmenting comprises a well-understood activity and comprises discreetly identifying specific organs or artifacts (and the external boundary of such structures) to thereby permit distinguishing one organ (or artifact) from another.

CT images often feature low contrast of soft tissues and the general appearance of treatment volumes on the one hand and organs-at-risk on the other hand often appear visually similar. The applicant has determined that deep learning techniques can provide useful results to support automatically segmenting a patient's breast tissue while non-deep learning techniques can provide useful results to support automatically segmenting a patient's organs-at-risk. (That said, the applicant has also determined that it can be useful to employ the imaging information 103 along with deep learning to automatically segment at least some heart tissue of the particular patient.)

Deep learning (also sometimes referred to as hierarchical learning, deep neural learning, or deep structured learning) is generally defined as a subset of machine learning in artificial intelligence that has networks capable of learning unsupervised from data that is unstructured or unlabeled. That said, deep learning can be also be supervised or semi-supervised if desired. Deep learning architectures include deep neural networks, deep belief networks, recurrent neural networks, and convolutional neural networks.

Deep learning employs multiple layers to progressively extract higher level features from raw input. In a typical configuration, each level learns to transform its input data into a more abstract and composite representation. As a simple example, in an image recognition application, the initial raw input may be a matrix of pixels, the first representational layer may abstract the pixels and encode edges, the second layer may compose and encode arrangements of those edges, the third layer may encode specific features such as nose and eyes, and the fourth layer may recognize that the image contains a face. Generally speaking, a deep learning process learns which features to optimally place in which level on its own.

By one approach the deep learning algorithm can be trained in a supervised learning setting using images and ground truth contours of several hundred patients. Useful data can be acquired, for example, from medical service providers across the globe. Images of the training set can be selected to represent a realistic spectrum of anatomical variety and typical image artifacts. If desired, ground truth contours can be created by human anatomy experts as part of the algorithm development.

While automated segmentation using traditional model and/or atlas-based algorithms can achieve expert-level performance, such performance has only been achieved with a small number of organs (thus requiring further human-based editing before being clinically acceptable). The inventors have determined that the foregoing deep learning-based approach can yield significantly better results by way of comparison, especially for structures without a well-defined learning setting using images and ground truth contours of several hundred patients.

At block 203, this process 200 provides for employing the imaging information 103 to also automatically determine a virtual-skin volume that corresponds to at least portions of the breast tissue 104 of the particular patient. By one approach, this activity can comprise using, at least in part, both the aforementioned three-dimensional CT imaging information and two-dimensional orthogonal topogram imaging information to determine the virtual-skin volume. (As used herein, the expression "virtual-skin volume" will be understood to mean a patient volume that is circumscribed by a calculated (and hence, "virtual") skin.)

In a typical radiation treatment application setting, the patient will lie or sit upon one or more patient support apparatuses 110 such as a couch, chair, armrest, or the like. In combination with the foregoing or in lieu thereof, one or more parts of the patient may be held in a fixed position by one or more patient fixation apparatuses 111. A patient fixation apparatus serves to hold some part of the patient in a fixed location during the administration of radiation in order to hold the treatment volume and/or organs-at-risk in a fixed location vis-à-vis the radiation source 115. Patient support apparatuses and patient fixation apparatuses are well understood in the art and require no further elaboration here.

With the foregoing in mind, at optional block 204 this process 200 can provide for automatically registering at least one of a patient support surface 110 and a patient fixation apparatus 111 to at least some of the imaging information 103 to provide corresponding resultant registration information. By one approach, automatically registering such an apparatus to the imaging information 103 can comprise automatically registering a model of at least one of the patient support surface and the patient fixation apparatus to at least some of the imaging information. "Registration" refers to aligning and bringing spatial correspondence between items. In this context, a representative model of the artifact at issue is aligned and brought into spatial correspondence with one or more features in the imaging information. The latter can then be employed as further input when automatically optimizing the radiation treatment plan as described below.

By another approach, in combination with the foregoing or in lieu thereof, at optional block 205 this process 200 employs the imaging information 103 to automatically determine a body outline for at least a portion of the patient. This body outline serves to represent an outermost physical boundary of the patient.

At block 206, this process 200 provides for employing at least the automatically segmented patient content as described above along with the virtual-skin volume as input 207 to a process for automatically optimizing a radiation treatment plan for the treatment volume 105 of this particular patient to thereby provide an optimized radiation treatment plan 113 for this patient.

Various approaches to optimizing a radiation treatment plan are known in the art. It can be noted, however, that, as suggested above, the foregoing registration information 208 can also be employed as further input when automatically optimizing the radiation treatment plan.

At the conclusion of the optimization process, this process 200 yields an optimized radiation treatment plan 113 for the particular patient as represented at block 209. (As will be described below in more detail, this process 200 can in fact yield a plurality of treatment plans, including, for example, three plans that differ from one another with respect to their particular radiation delivery modality and technique.) If desired, and as shown at optional blocks 210 and 211, this process 200 can further include using the above-mentioned body outline, the virtual skin volume, and registration information as inputs to automatically calculate radiation treatment platform trajectories, collision detection, and virtual dry run information of treatment delivery per the optimized radiation treatment plan 113.

It should be understood that these plans are ready-to-use and accordingly can be used to administer radiation to the patient via the aforementioned platform. By one approach at least one such resultant plan is, in fact, then utilized to deliver therapeutic radiation to treat the patient's treatment volume.

Figure 3:
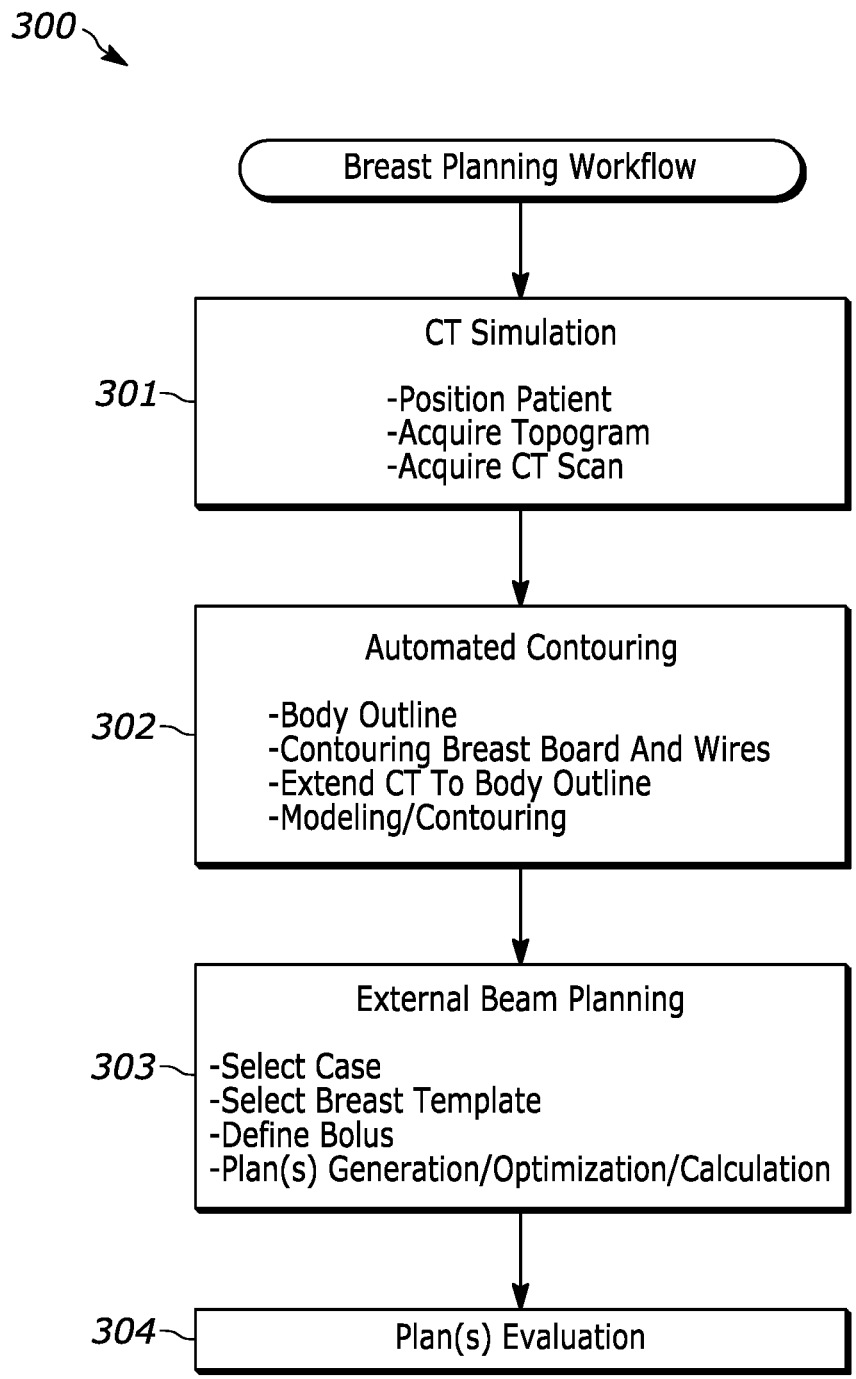
FIG. 3 comprises a flow diagram as configured in accordance with various embodiments of these teachings.

Referring now to FIG. 3, a particular instantiation of these teachings will be presented. For the sake of an illustrative example FIG. 3 presents this process 300 in the context of a breast planning workflow (i.e., a workflow to develop an administrable beam-based radiation therapy to treat a treatment volume 105 comprising a cancer tumor in the breast tissue 104 of a particular patient). It will be understood that the specific details of this example are intended to serve an illustrative purpose and are not intended to suggest any particular limitations as regards these teachings.

At block 301 this process 300 begins the workflow with CT images. After appropriately positioning the patient on a breast board in accordance with well understood prior art practice, this activity includes acquiring at least one topogram and one CT scan. By one approach, the former comprises acquiring at least two orthogonal topograms that include the patient's arms and the breast board with as wide a field of view as possible given the available equipment and other limitations of the application setting. By one approach the at least one CT scan includes scans looking superiorly to include a slice above the patient's shoulder and looking inferiorly below the patient's breast tissue 104 as well as scans that include the treatment volume 105. In a typical application setting, these images are in a digital format as described earlier.

Generally speaking, the equipment and processes utilized to acquire these topogram and CT scan images are well understood in the prior art. Although the particular views acquired and the follow-on use described herein does not necessarily accord with prior art practice, for the sake of brevity no further elaboration is needed here as regards the acquisition of the images themselves.

At block 302, the foregoing images are imported to an automated contouring activity. Contouring, of course, comprises identifying and/or specifying the outline of individual organs, tissues, or other anatomical structures and artifacts of the patient such as, but not limited to, part or all of the patient's breast tissue, the patient's lungs, heart, and/or chest wall. This contouring activity includes, for example, automatically contouring the patient's body outline excluding the breast board and any attendant wires/conductors that may be present. By another approach, in lieu of the foregoing or in combination therewith, this contouring activity includes automatically contouring the breast board and/or foregoing wires/conductors separate and apart from other image content.

By one approach, this activity can include extending available CT imagery to extend outwardly and thereby include the patient's exterior body outline. So configured, the CT image content can be extended to include the outer boundary of the patient's torso, neck, and/or part or all of the patient's arms.

By one approach this automated contouring activity makes use of relevant models. For example, a relevant model of a breast board and/or a patient support couch can be employed to assist in these regards.

At block 303, and following the foregoing contouring activity, this process 300 provides for external beam planning. By one approach, if desired, this external beam planning activity can include automatic or user-initiated use of a breast plan creation wizard. (It will be understood that a wizard comprises software that automates a complex task by asking the user a series of easy-to-answer questions, which answers then drive the customized execution of the task.)

Based upon the contouring information, this block 303 can include automatically selecting whether the delineated treatment target (or targets) present a left breast case, a right breast case, or a bilateral breast case. This selection can be based, for example, upon structure coding that is assigned during the contouring process. (If desired, this process 300 will accommodate presenting the technician with an opportunity to override and change this automated selection.) Generally speaking, this process also includes automatically defining a particular patient orientation. That said, if desired, an opportunity can be provided to permit the attending technician to select the inclusion of lymphatic nodes.

This process then provides for automatically selecting a particular starting point breast treatment template. This selection can be based upon various criteria. By one approach this criteria includes the patient's clinical goals (including, as appropriate, any established ordering and/or prioritization of such goals). By one approach this criteria includes the relevant dose prescription, identification of a default linac, and/or any energy specifications (where the latter can be automatically defined or user-specified or overridden as desired). By yet another approach this criteria can include bolus specifications (including, for example, any corresponding fractional amounts). By yet another approach, this criteria can include sizing information (for example, in millimeters or centimeters) for skin flash. And as yet by another approach, this criteria can include information that specifies a particular RapidPlan™ (RP) model to facilitate predicting the dose volume histogram.

When taking the bolus into account, if desired this process can include opening a display window on a user interface to facilitate defining the bolus. By one approach this process will accommodate defining a bolus for only some fractions rather than all. When only some fractions have a bolus, by one approach this planning activity can automatically serve to create at least six corresponding plans. (A "fraction" refers to only a portion of a total dose represented, for example, by a dose administered from a particular angle or field of view.)

This activity includes selecting a particular imaging template and automatically creating corresponding set up fields that can be used as an initial starting point for treatment using a particular accelerator. Examples include but are not limited to cone beam computed tomography (CBCT), megavolt (MV), and kilovolt (kV).

In this example, external beam planning includes generating, optimizing, and calculating three plans (or, when utilizing a bolus for some fractions, six plans). These plans include a TO-VMAT (trajectory optimizer-volumetric-modulated arc therapy) plan, a TO-IMRT (trajectory optimizer-intensity-modulated radiation therapy) plan, and an iComp irregular surface compensator plan. These different plans utilize different techniques as specified. These teachings will also accommodate other techniques such as, for example, a hybrid combination of VMAT and IMRT or a hybrid combination of open fields with IMRT if desired.

The geometry definition of the VMAT arcs and IMRT fields use a trajectory optimizer (TO) that supports dynamic or static collimator angle determination, coplanar and non-coplanar fields, energy selection, and isocenter placement. (Those skilled in the art will recognize that trajectory optimization is an expansion on trajectory optimization in radiotherapy using sectioning as it is understood in the art.) In particular, the field order is tuned for plan quality, collision prevention, and efficient delivery. Gantry slow down for arcs, restricted leaf sequences, and modified control point weights are additional modifications that these teachings will accommodate to help improve plan quality.

Optimizing leaf sequences and fluence can take the defined skin flash margin into account to address possible target change or movement if desired.

The geometry definition of irregular surface compensator planning can be based on the contoured target volume including isocenter placement. Optimization of the fluence can be done taking the prioritized physician clinical goal into account by minimizing dosing for the defined organs at risk while maintaining desired coverage of the target volume. By one approach, predefined size of skin flash margin can be automatically added to the fluence to address possible target change or movement in the plan. Leaf motion calculation and dose calculation can be done automatically once the fluence is optimized.

If desired, automatic interactive optimization for volumetric modulated arc therapy planning (as is understood in the art) can be utilized during the optimization process for some or all of the plans to achieve Pareto optimal optimized dosing.

TO-VMAT Plan Creation

This process can automatically optimize radiation source trajectories by defining one or more arcs and collimator positions as a function of ordering consideration of one or more organs at risk in the breast template and the patient treatment volume (the latter considered with or without nodes as desired and/or specified). By one approach collision detection can run in the background to check that trajectories are collusion free. By one approach the available clinical goals are translated into optimization objectives, which objectives are then utilized to guide the iterative optimization process. By one approach the accelerator photon energy is defined.

Following plan optimization, this process can calculate the administered dose.

TO-IMRT Plan Creation

This process can automatically optimize radiation source trajectories, at least in part, by defining the static fields as a function of ordering consideration of one or more organs at risk in the breast template and the patient treatment volume (the latter considered with or without nodes as desired and/or specified). By one approach collision detection can run in the background to check that trajectories are collusion free. By one approach the available clinical goals are translated into optimization objectives, which objectives are then utilized to guide the iterative optimization process. By one approach the energy is defined.

Following plan optimization, this process can calculate leaf motions for employed multi-leaf collimators as well as administered dose.

iComp Plan Creation

This process can automatically specify tangential fields based upon the patient's treatment volume. Such fields are parallel opposed fields. The number of fields will usually depend on the size of the target. While using two fields will often suffice, additional fields may be added. If the lymph nodes are included, additional abutting fields are sometimes added to facilitate treatment of the nodes. By one approach collision detection can run in the background to check that trajectories are collusion free. By one approach the available clinical goals are translated into optimization objectives, which objectives are then utilized to guide the iterative optimization process. By one approach the energy is defined.

Calculating collision-free geometry can be based on the patient geometry relative to the treatment couch and fixation device(s) in the relevant gantry arc plane. By one approach and imaging-based model supports calculating the collision zone. Using this approach permits automatically searching for and generating more complex trajectories that may, in turn, improve plan quality and efficacy.

Following plan optimization, this process can calculate leaf motions for employed multi-leaf collimators as well as administered dose.

At block 304 this process 300 provides for evaluating the foregoing plan or plans. Again, in a typical application setting, the foregoing process provides three separate plans (or six when selecting a bolus for some fractions). By one approach, none of the results are presented for the technician's consideration until all of the plans are ready.

By one approach, this evaluation includes presenting the calculated results of all three breast plans, where the calculations represent the results corresponding to the prioritized physician intent and other metrics of concern (such as the heterogeneity index (HI), gradient index (GI), monitor units, modulation complexity, and treatment time). When presenting double plans that account for the presence of bolus, a plan sum can be created each time for the plan with and without a bolus. In any event, all three breast sum plans can be presented with a score based on corresponding clinical goals and other metrics of interest. That score may comprise, for example, a pass/fail indication for each clinical goal.

So configured, the technician can review the proffered plans and identify a most optimal plan for that patient. This, in turn, can lead to approving a particular plan for this particular patient.

If desired, these teachings will accommodate permitting the technician to conduct a virtual dry run of the treatment delivery of the defined treatment fields via a 3-D animation. This virtual dry run can comprise a representation of the treatment delivery using the actual treatment machine, couch, fixation device, and patient dimensions. If desired, a mountain view gives an indication of the clearance between the patient and application setting machinery and/or clearance between each machine during the treatment delivery.

Figure 4:
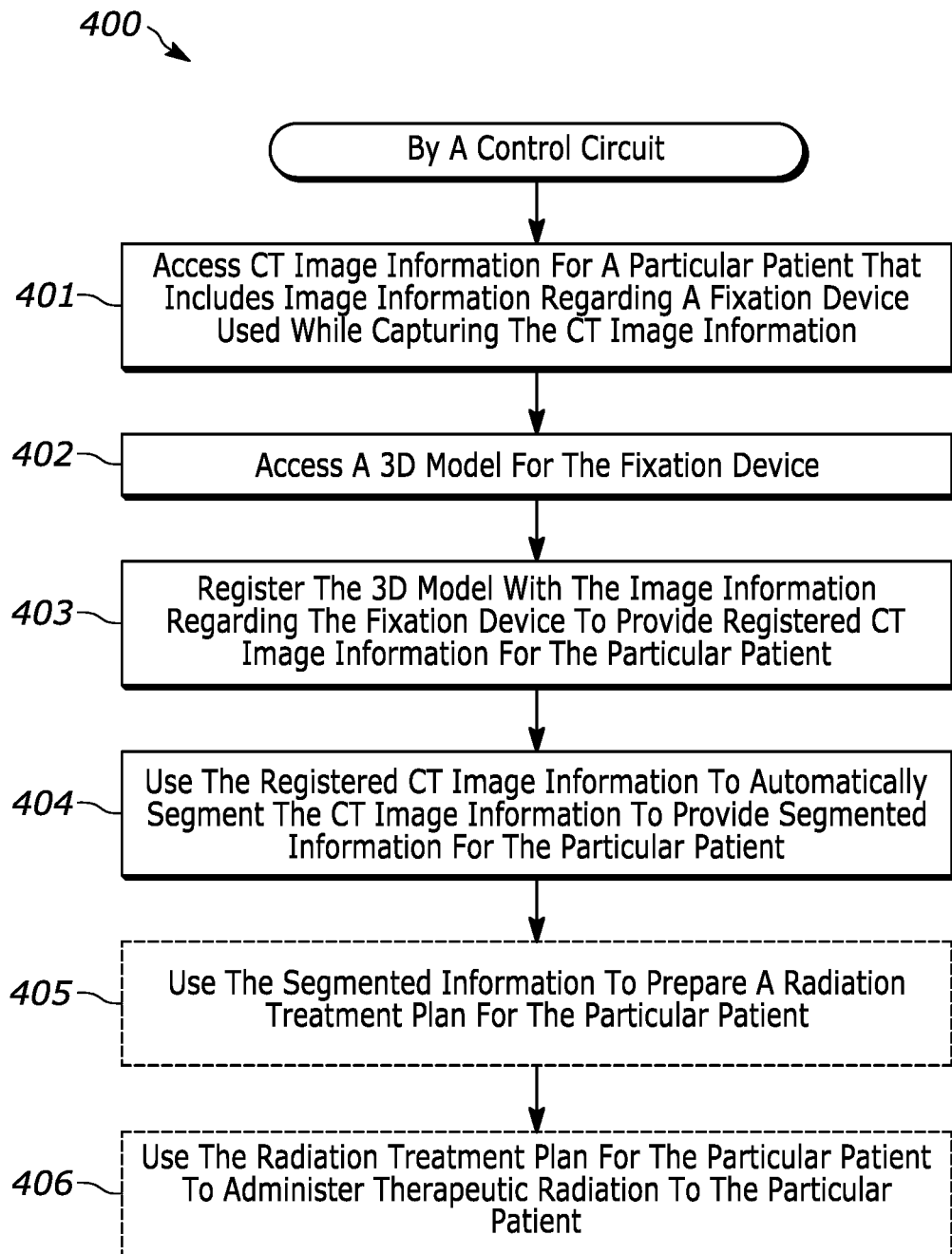
FIG. 4 comprises a flow diagram as configured in accordance with various embodiments of these teachings.

Referring now to FIG. 4, a particular process 400 for accommodating image information regarding a fixation device 111 in CT image information for a patient will be described. It shall be understood that the specifics of this described process are intended to serve an illustrative purpose and are not intended to suggest any particular limitations as regards these teachings.

Also, and for the sake of this illustrative example, the following description presumes that the described activities are carried out by a control circuit 101 of choice.

At block 401 this process 400 provides for accessing computed tomography (CT) imaging information 103 for a particular patient wherein the CT image information includes image information regarding a patient fixation device 111 that serves to immobilize at least a portion of the particular patient (such as the aforementioned breast tissue 104) while capturing the CT image information. In this illustrative example the fixation device 111 comprises a plurality of structural elements that are capable of movement relative one another. One such structural element may comprise, for example, a base plate configured to rest flat atop a corresponding support surface.

Figure 5:
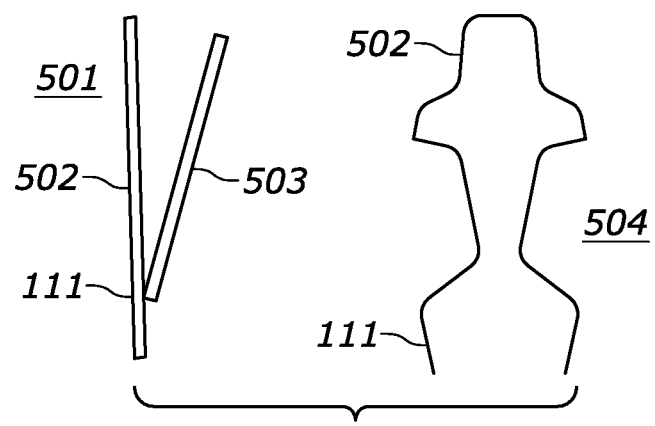
FIG. 5 comprises a simplified schematic view as configured in accordance with prior art practice.

FIG. 5 provides an illustrative example in these regards, wherein a first CT image 501 presents a side view of the fixation apparatus 111. For the sake of simplicity and clarity, in this schematic representation the patient fixation apparatus 111 comprises a base plate 502 and a pivoting member 503 that pivotally connects to the base plate 502 and can selectively pivot with respect thereto. A second CT image 504 presents a bottom view of the fixation apparatus 111 and in particular depicts the base plate 502. It will be understood that in a typical application setting such images 501 and 504 will also include image content for various tissues and structures in the patient themselves. Such patient-based image content is not shown here for the sake of clarity.

At block 402, this process 400 provides for accessing a three-dimensional (3-D) model for the fixation device 111. By one approach the control circuit 101 accesses the above-mentioned memory 102 to thereby access this 3-D model. This activity can include combining the 3-D model information with the aforementioned CT image(s).

Figure 6:
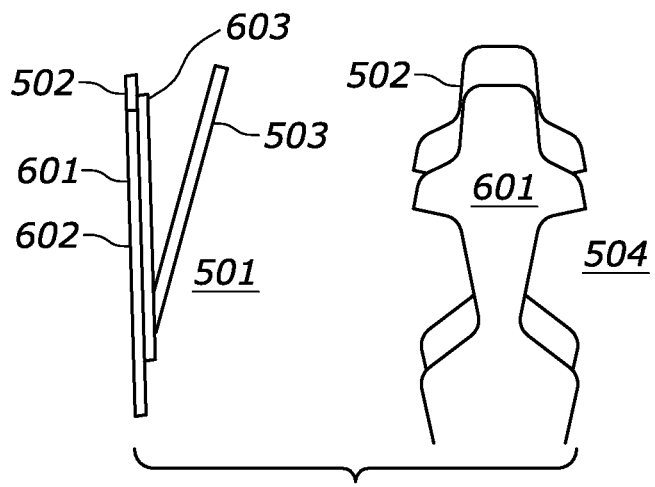
FIG. 6 comprises a simplified schematic view as configured in accordance with various embodiments of these teachings.

FIG. 6 provides an illustrative example in these regards. In this example the model 601 is overlaid on top of at least a portion of the corresponding image of the fixation device 111. In this simple example, the base plate 602 of the model 601 mostly but not completely overlies the pixels for the base plate 502 of the fixation device 111 image. The pivotal member 603 of the model 601 is disposed parallel to the base plate 602. (It will be understood that the original placement of the 3-D model images in the CT images may not result in the orientations show. Instead, the model imagery may be more distant from the CT imagery of the fixation device 111, in which case the model imagery would require some movement in order to better align and register with the CT imagery of the fixation device 111.)

At block 403 this process 400 provides for registering the 3-D model for the fixation device with the pixels of the image information regarding the fixation device to provide registered CT image information for the particular patient.

These teachings will accommodate a variety of approaches in these regards. By one approach, for example, this registration activity can comprise, at least in part, registering the plurality of structural elements in seriatim manner. When dealing with a fixation device 111 having a base plate, this seriatim approach can begin by first registering the base plate (i.e., moving the image of the 3-D model base plate 602 until it registers with the CT image of the base plate 502). Beginning with the base plate can be advantageous at least because the base plate will typically have a known orientation (such as 0° with respect to some known reference orientation). The resultant reduction in dimensionality can ease the process of locating and registering with the base plate in the CT image.

Other modeled structural elements can then be registered with their corresponding structural element CT images in a given desired order. For example, if a particular fixation device 111 featured a base plate, a first pivoting member that pivotally attached to that base plate, and a second pivoting member that pivotally attached to the first pivoting member, the foregoing approach could provide for first registering the base plate, and then, following complete registration of the base plate, then registering the first pivoting member, and finally the third pivoting member.

Generally speaking, by one approach the 3-D model for the fixation device can include rules that specify rules of movement for each of the plurality of structural elements that are capable of movement relative one another. For example, at least one such rule of movement could specify a range of permitted movement such as a permitted number of degrees that one structural element can pivot with respect to another.

As another example, at least one such rule of movement can specify a linear translation of a first one of the plurality of structural elements with respect to a second one of the plurality of structural elements. By one approach, the rules of movement can specify such linear translation by specifying linear translation of a first one of the plurality of structural elements along a vector defined by two points belonging to a second one of the plurality of structural elements.

As yet another example, at least one such rule of movement can specify rotation of a first one of the plurality of structural elements with respect to a second one of the plurality of structural elements. Such a rule would be useful in the present illustrative example where the one member 503 can move pivotally with respect to a base plate 502. By one approach, the rules of movement can specify such rotation by specifying rotation of a first one of the plurality of structural elements around a vector that is defined by two points belonging to the second one of the plurality of structural elements.

Figure 7:
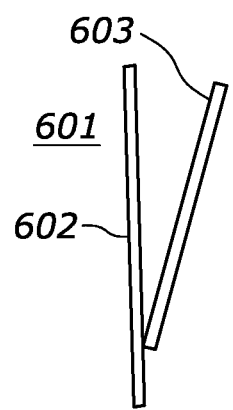
FIG. 7 comprises a simplified schematic view as configured in accordance with various embodiments of these teachings.
Figure 8:
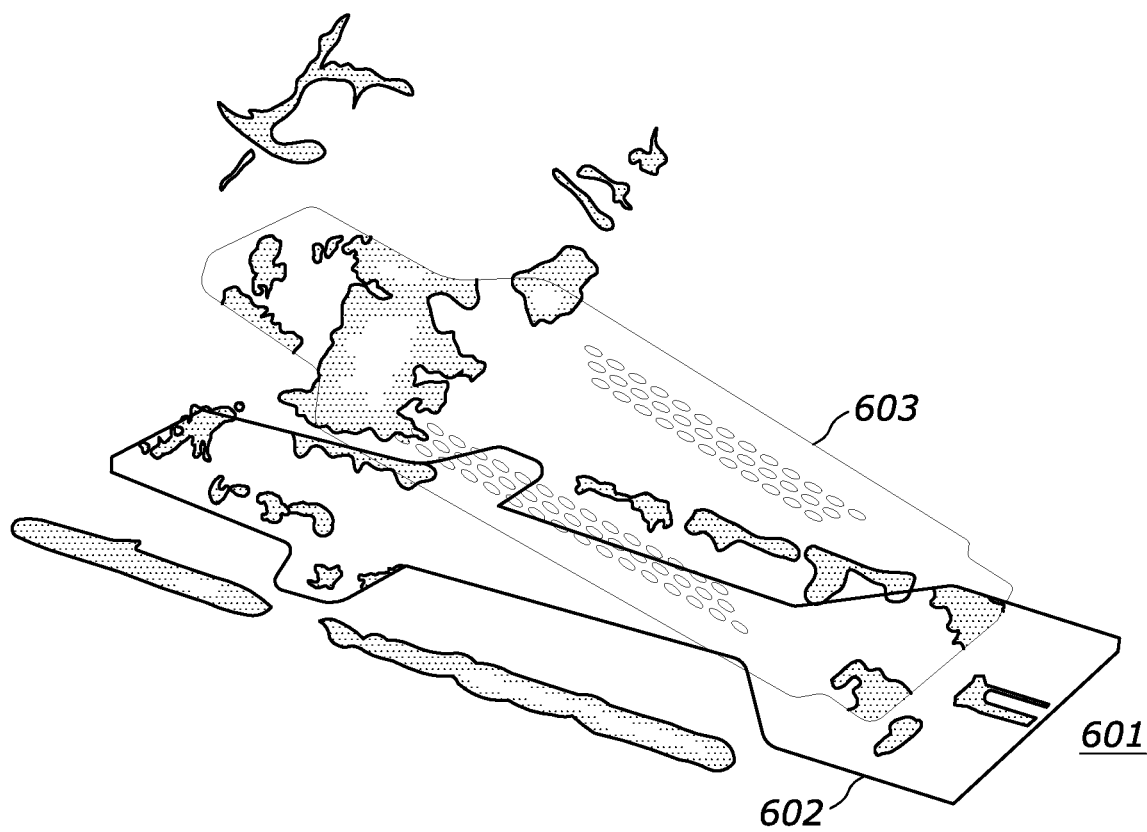
FIG. 8 comprises a simplified perspective schematic view as configured in accordance with various embodiments of these teachings.

So configured, and referring momentarily to FIG. 7, the image of the 3-D model 601 can fully register with the pixels of the CT image of the fixation device 111. In the simple example of FIG. 7, the registration is perfect and hence the image of the 3-D model 601 fully overlays and hence occludes the CT image of the fixation device 111. FIG. 8 offers another example in these same regards. In FIG. 8, the 3-D model image 601 is shown as a perspective rendering in conjunction with some other patient-based imagery that appears in the original CT image.

Referring again to FIG. 4, at block 404 the control circuit 101 uses the resultant registered CT image information for the particular patient to automatically segment the CT image information for the particular patient to provide segmented information for the particular patient. Those skilled in the art will appreciate that such automated segmentation can be carried out with greater efficiency and accuracy when the segmentation analysis can be assured of the nature and location of the fixation device in the CT image.

At block 405, if desired, this process 400 can use the foregoing segmented information for the particular patient to prepare a radiation treatment plan 113 for the particular patient. At block 406, and again if desired, this process 400 can provide for using the aforementioned radiation treatment plan for the particular patient to administer therapeutic radiation to the particular patient using the above-described radiation treatment platform 114.

Those skilled in the art will recognize that a wide variety of modifications, alterations, and combinations can be made with respect to the above described embodiments without departing from the scope of the invention. As one example in those regards, the foregoing process could be utilized during a treatment session while administering radiation to a patient. Accordingly, such modifications, alterations, and combinations are to be viewed as being within the ambit of the inventive concept.

What is claimed is:

1. A method comprising:
accessing computed tomography (CT) image information for a particular patient wherein the CT image information includes image information regarding a fixation device that served to immobilize at least a portion of the particular patient while capturing the CT image information;
accessing a three-dimensional (3D) model for the fixation device;
combining information regarding the 3D model for the fixation device with the image information regarding the fixation device to provide combined CT image information for the particular patient;
preparing a radiation treatment plan for the particular patient as a function, at least in part, of the combined CT image information for the particular patient.

2. The method of claim 1 wherein the CT image information includes image information regarding a plurality of fixation devices that each served to immobilize at least a corresponding portion of the particular patient while capturing the CT image information.

3. The method of claim 1 further comprising, before combining the information regarding the 3D model for the fixation device with the image information regarding the fixation device, moving at least one part of imagery for the 3D model with respect to another part of the imagery for the 3D model.

4. The method of claim 3 wherein moving at least one part of imagery for the 3D model with respect to another part of the imagery for the 3D model comprises moving the at least one part with respect to the another part as a function of at least one rule governing such movement.

5. The method of claim 1 wherein combining the information regarding the 3D model for the fixation device with the image information regarding the fixation device comprises:
moving imagery for the 3D model as a whole with respect to the CT image information to provide moved 3D model imagery;
moving imagery for part, but not all, of the moved 3D model imagery with respect to the CT image information.

6. The method of claim 1 further comprising:
using the combined CT image information for the particular patient to automatically segment the CT image information for the particular patient to provide segmented information for the particular patient.

7. The method of claim 1 wherein the 3D model for the fixation device comprises, at least in part, rules of movement for portions of the fixation device.

8. The method of claim 7 wherein the rules of movement for portions of the fixation device comprise at least one rule specifying a range of permitted movement.

9. The method of claim 7 wherein the rules of movement for portions of the fixation device comprise at least one rule specifying a linear translation of a first portion of the fixation device with respect to a second portion of the fixation device.

10. The method of claim 1 further comprising:
using the radiation treatment plan for the particular patient to administer therapeutic radiation to the particular patient.

11. An apparatus comprising:
a control circuit configured and arranged to:
access computed tomography (CT) image information for a particular patient wherein the CT image information includes image information regarding a fixation device that served to immobilize at least a portion of the particular patient while capturing the CT image information;
access a three-dimensional (3D) model for the fixation device;
combine information regarding the 3D model for the fixation device with the image information regarding the fixation device to provide combined CT image information for the particular patient;
prepare a radiation treatment plan for the particular patient as a function, at least in part, of the combined CT image information for the particular patient.

12. The apparatus of claim 11 wherein the CT image information includes image information regarding a plurality of fixation devices that each served to immobilize at least a corresponding portion of the particular patient while capturing the CT image information.

13. The apparatus of claim 11 wherein the control circuit is further configured and arranged to, before combining the information regarding the 3D model for the fixation device with the image information regarding the fixation device, move at least one part of imagery for the 3D model with respect to another part of the imagery for the 3D model.

14. The apparatus of claim 13 wherein the control circuit is configured and arranged to move at least one part of imagery for the 3D model with respect to another part of the imagery for the 3D model by moving the at least one part with respect to the another part as a function of at least one rule governing such movement.

15. The apparatus of claim 11 wherein the control circuit is configured and arranged to combine the information regarding the 3D model for the fixation device with the image information regarding the fixation device by:
moving imagery for the 3D model as a whole with respect to the CT image information to provide moved 3D model imagery;

moving imagery for part, but not all, of the moved 3D model imagery with respect to the CT image information.

16. The apparatus of claim 11 wherein the control circuit is further configured and arranged to:
use the combined CT image information for the particular patient to automatically segment the CT image information for the particular patient to provide segmented information for the particular patient.

17. The apparatus of claim 11 wherein the 3D model for the fixation device comprises, at least in part, rules of movement for portions of the fixation device.

18. The apparatus of claim 17 wherein the rules of movement for portions of the fixation device comprise at least one rule specifying a range of permitted movement.

19. The apparatus of claim 17 wherein the rules of movement for portions of the fixation device comprise at least one rule specifying a linear translation of a first portion of the fixation device with respect to a second portion of the fixation device.

20. The apparatus of claim 11 wherein the control circuit is further configured and arranged to:
use the radiation treatment plan for the particular patient to administer therapeutic radiation to the particular patient.

* * * * *